US007172632B2

(12) United States Patent
Smith et al.

(10) Patent No.: US 7,172,632 B2
(45) Date of Patent: Feb. 6, 2007

(54) HAIR COLORING COMPOSITIONS

(75) Inventors: Liam Robert Smith, Nottingham (GB); Stewart Paul Long, Nottingham (GB)

(73) Assignee: The Boots Company, PLC, Nottingham (GB)

( * ) Notice: Subject to any disclaimer, the term of this patent is extended or adjusted under 35 U.S.C. 154(b) by 261 days.

(21) Appl. No.: 10/486,577

(22) PCT Filed: Jul. 31, 2002

(86) PCT No.: PCT/GB02/03492

§ 371 (c)(1),
(2), (4) Date: Feb. 11, 2004

(87) PCT Pub. No.: WO03/015734

PCT Pub. Date: Feb. 27, 2003

(65) Prior Publication Data

US 2005/0039269 A1    Feb. 24, 2005

(30) Foreign Application Priority Data

Aug. 16, 2001 (GB) ................................ 0120006.2

(51) Int. Cl.
*A61K 7/13*    (2006.01)
(52) U.S. Cl. ....................... 8/405; 8/406; 8/410; 8/421; 424/74
(58) Field of Classification Search .................... 8/405, 8/406, 410, 421; 424/74
See application file for complete search history.

(56) References Cited

U.S. PATENT DOCUMENTS 4,933,177 A * 6/1990 Grollier et al. ............... 424/74
5,620,484 A * 4/1997 Maubru ........................ 8/409
5,686,082 A   11/1997 Auang-Lan N'Guyen
6,060,061 A    5/2000 Breton et al.
6,099,591 A    8/2000 Cornuelle et al.
6,855,312 B1 * 2/2005 Craig et al. .................. 424/745

FOREIGN PATENT DOCUMENTS

| EP | 0 776 652 A | 6/1997 |
|----|-------------|--------|
| EP | 1142563 A | 10/2001 |
| FR | 2 527 927 A | 12/1983 |
| WO | 0 968 709 A | 1/2000 |
| WO | WO 01 06997 A | 2/2001 |

OTHER PUBLICATIONS

Database WPI Week 199830, Derwent Publications Ltd., AN 1998—343186 & JP 10 130129A.
Database Caplus Online!, Chemical Abstracts Service, Database accesion No. 1999:699068 & JP 11 302138A.
Patent Abstracts of Japan, vol. 2003, No. 01 (C, Jan. 14, 1903 & JP 2002 255766 A. & Database Caplus Online! Chemical Abstracts Services.

* cited by examiner

*Primary Examiner*—Eisa Elhilo
(74) *Attorney, Agent, or Firm*—Rothwell, Figg, Ernst & Manbeck, P.C.

(57) ABSTRACT

A hair coloring composition contains an oxidative hair dye and at least one antioxidant agent selected from the group consisting of *rosmarinus officinalis, origanum vulgare, camellia sinensis, camellia oleifera, salvia officinalis, apium graveolen, thymus vulgaris, rosa canina* and *coriandrum sativum* in combination with a suitable diluent or carrier. The hair coloring compositions are gentler on the skin and hair in that they reduce the effects or the oxidising agent on the hair and skin.

20 Claims, No Drawings

HAIR COLORING COMPOSITIONS

CROSS REFERENCE TO RELATED APPLICATION

This application is a 35 USC § 371 National Phase Entry Application from PCT/GB02/03492, filed Jul. 31, 2002, and designating the U.S.

The present invention relates to compositions used to colour the hair and to methods of using such compositions to treat the hair.

The term "hair colouring composition" as used herein comprises any composition which includes means semi-permanently or permanently to colour, tint and/or dye the hair. Such compositions include so-called shampoos, conditioners, hair dyes, mousses, foams, gels, creams, lotions and rinses, all comprising means to semi-permanently and permanently colour the hair, and all suitable for use on animals, especially on humans, and most particularly on the human head.

Compositions which are used to deliver permanent and semi-permanent colour to the hair, via an oxidative mechanism, are required to be in the form of a two component composition. One component, which may be a shampoo or conditioner type formulation, carries the dye molecules, and the other component, which may be described as a developing lotion, carries an oxidising agent, eg hydrogen peroxide.

Prior art compositions used to colour the hair have various disadvantages. The new colour fades after, typically, six to eight subsequent washes of the hair for semi-permanent and twenty to twenty-four washes of the hair for permanents. The regrowth of the hair from the roots also reveals the natural colour of the hair, and requires recolouring of the hair to avoid this. Thus, to retain the new colour repeated treatment with hair colouring is required. This is inconvenient and expensive. The ingredients used in many hair colouring compositions are often noxious and therefore it may also be desirable to reduce the number of times hair is exposed to such compositions and/or to reduce or remove the more noxious ingredients from such hair colouring compositions. Semipermanent and permanent hair colours work by a process of oxidation, and this can lead to oxidation of the hair's lipids and proteins. This is undesirable and can lead to degradation in the hair's condition.

Therefore it is an object of the present invention to overcome some or all of the aforementioned disadvantages, and in particular to provide hair colouring compositions which are gentler and milder to the hair.

According to the invention, there is provided a hair colouring composition containing an oxidative hair dye and at least one antioxidant agent selected from the group consisting of
*rosmarinus officinalis;*
*origanum vulgare;*
*camellia sinensis;*
*camellia oleifera;*
*salvia officinalis;*
*apium graveolens;*
*thymus vulgaris;*
*rosa canina;* and
*coriandrum sativum* in combination with a suitable diluent or carrier.

In the process of providing a permanent or semi-permanent colour to the hair, it is required to oxidise the dye molecules so that they react into the complex dyestuffs that reside in the hair. Hydrogen peroxide is an example of such an oxidant, and is used to initiate the oxidation of the intermediate molecules. Also susceptible to oxidation are the lipids on the surface of the hair and the proteins on and within it. Oxidation of such proteins or the removal of them will lead to a reduction in hair strength. The oxidation of the hair lipids and proteins can follow a chain reaction mechanism, by which hydrogen peroxide is the initiator, and oxidised protein and lipoperoxide are typical products. The hydrogen peroxide molecules degenerate into reactive oxygen species, which are free radicals, and rapidly start the chain reactions mentioned previously.

One way of preventing the oxidative damage would be to use free radical scavenging agents, eg antioxidants, to mop up the reactive oxygen species, preventing the chain reactions. A disadvantage would be that the free radical scavengers may also mop up the reactive dye intermediate once they had been oxidised, and this would prevent dye stuff formation.

To overcome this problem, the present invention is used. The present invention relates to the use of anti-oxidants that may be referred to as "chain-breaking", since they are believed to block the chain reactions mentioned above from developing far enough to produce lipoperoxide and oxidised proteins on the hair surface and the removal of protein from the hair's structure, but do not inhibit the development of colour on the hair by mopping up the reactive radical dye molecules after oxidation. Incorporation into the dye formulation or the developing lotion of the product of the "chain-breaking" antioxidants has been shown to reduce considerably and significantly the levels of lipid and protein peroxidation on and in the hair surface and during hair colouring with a semi-permanent or permanent hair colouring.

The composition according to the invention may contain a single one of the chain-breaking antioxidants. However, the antioxidants have shown significant synergistic action in combination with each other, enhancing the protection of the hair against oxidative damage. This action is shown to be present with no adverse effect on the colour obtained on the hair.

Where the composition contains a single one of the chain-breaking antioxidants, that antioxidant is preferably selected from a preferred, first group of the following antioxidants:
*origanum vulgare;*
*camellia sinensis;*
*camellia oleifera;*
*apium graveolens;* and
*salvia officinalis.*

Alternatively, the antioxidant may be one of a second group:
*rosmarinus officinalis;*
*thymus vulgaris;*
*rosa canina;* and
*coriandrum sativum.*

Particularly preferred antioxidants for single use, ie for use in compositions that are free of any of the other antioxidants are:
*origanum vulgare;*
*camellia sinensis*
*camellia oleifera;* and
*apium graveolens.*

Where two of the antioxidants are used in combination, the antioxidants are preferably one from the first group and one from the second group. A particularly preferred antioxidant from the first group is *origanum vulgare*, which is most preferably used in combination with either *rosa canina* or *thymus vulgaris* from the second group.

The composition most preferably comprises three of the antioxidants named above. In such a case, the composition is preferably free of other antioxidants.

Where three of the antioxidants are used in combination, then the antioxidants most preferably include one or two from the first group and two or one respectively from the second group.

It is particularly preferred that the composition should include one antioxidant from the first group and two from the second group. The two antioxidants from the second group are preferably selected from *rosa canina, coriandrum sativum* and *thymus vulgaris*.

Particularly preferred combinations are combinations of one of
*camellia oleifera;*
*camellia sinensis;*
*salvia officinalis;* and
*origanum vulgare;* with two of
*rosa canina;*
*thymus vulgaris;* and
*coriandrum sativum.*

Particularly preferred combinations of antioxidants are:
*camellia oleifera/rosa canina/thymus vulgaris*
*camellia sinensis/rosa canina/coriandrum sativum*
*salvia officinalis/coriandrum sativum/thymus vulgaris;* and
*origanum vulgare/coriandrum sativum/thymus vulgaris.*

The first of the above four combinations is especially preferred.

Suitable hairs dyes for use in the hair colouring compositions of the present invention include:
p-amino phenol, p-phenylenediamine, 4-chlororesorcinol, resorcinol, p-amino-o-cresol, m-aminophenol, p-toluenediamine sulphate, N,N-bis(hydroxyethyl-p-phenylenediamine) sulphate, 2,5-diamine toluene sulphate, 4-amino-2-hydroxy toluene, 2-amino 4-hydroxyethylaminoanisole sulphate, o-chloro-p-phenylenediamine sulphate, 4-nitro-m-phenylenediamine, n-phenyl-p-phenylenediamine, n-phenyl-p-phenylenediamine sulphate, 1-naphthol, 6-chloro-2-amino-4-nitrophenol, 2-amino-3-hydroxy pyridine, 4-amino-3-nitrophenol, 4-amino-m-cresol, 2-methyl-5-hydroxyethylaminophenol, 6-hydroxyindole, 2-methyl resorcinol, 5-amino-6-chloro-o-cresol, 1-phenyl-3-methyl-5-pyrazolone, 4-hydroxypropylamino-2-nitrophenol, 4-hydroxyethlamino-2-nitrophenol, 2,6 diaminopyridine, m-phenylenediamine, p-aminophenol sulphate, m-aminophenol sulphate, phenyl methyl pyrazolone, 2,4-diaminophenoxyethanol HCl, t-butylhydroquinone, p-methyl aminophenol sulphate, 2-amino-3-hydroxypyridine, 4-amino-2-hydroxytoluene, p-methyl aminophenol sulphate, 2,6-dihydroxy-3,4-dimethylpuridine, 1,2-bis-(2,4-diaminophenoxy) propane or 1,5-naphthalenediol.

The particular hair dye and the amount present will depend on the colorant effect that is desired. The hair dyes may be used in combination to provide the desired shade.

The effectiveness of the antioxidants used in the present invention in inhibiting lipoperoxidation may be demonstrated by the following in vitro and ex vivo methods:

In vivo Method

Hair lipids were extracted, using chloroform/methanol, and then this lipid was subjected to oxidative attack, both with and without the presence of the antioxidant species. A colourimetric assay was used to detect lipid peroxide with methyl blue, and these levels were quantified using a spectrophotometer.

Ex vivo Method

Hair swatches were dyed, with and without the presence of the antioxidant species, and then the lipids were extracted from the hair with chloroform/methanol. Care was taken to ensure that dye molecules were not also removed which would then interfere with the assay results.

Methods are as follows:
1. Lipid was extracted from the hair.
2. The supernatant was then dispensed and dried down to leave lipid.
3. The lipid was then exposed to peroxide solution with and without antioxidant.
4. Chloroform/methanol was added. This formed an organic layer underneath the aqueous peroxide solution. This drew the lipid from the aqueous solution into the organic layer.
5. The organic layer was removed and dried down under vacuum.
6. The lipid was the resuspended in methanol and assayed.

When lipids are extracted from dyed hair, chloroform/methanol is used to extract directly from the hair and the method follows as above.

Where a single antioxidant is present in the composition, the level of lipid peroxidation inhibition is preferably greater than 40%, more preferably greater than 50%, or greater than 60%.

Where two or three of the antioxidants are present, the inhibition of lipid peroxidation is preferably greater than 60%, and may be greater than 70% or greater than 80%.

The hair colouring compositions of the present invention are gentler on the skin and hair in that they comprise hydrogen peroxide ($H_2O_2$) and/or ammonia ($NH_3$) in combination with the specified antioxidants, which reduce the effects of the oxidising agent on the hair and skin.

The antioxidants used in the present invention are plant extracts, which have significant flavenoid content:
Rosemary—*rosmarinus officinalis*—(for example the Provital product as supplied by S Black Ltd, Foxholes Business Park, John Tate Road, Hertford, Herts, SG13 7YH, United Kingdom),
Oregano—*origanum vulgare*—(for),
Green Tea—*camellia sinensis*—(for example as supplied by Nichemein Europe PLC, Am Wehrhan 333, Dusseldorf, Germany),
Japanese Green Tea—*camellia oleifera*—(for example as supplied by Fragrance Oils (International) Ltd, Eton Hill Industrial Estate, Eton Hill Road, Radcliffe, Manchester, M26 9XT, United Kingdom),
Sage—*salvia officinalis*—(for example as supplied by Fragrance Oils (International) Ltd),
Celery—*apium graveolens*—(for example as supplied by Fragrance Oils (International) Ltd),
Coriander—*coriandrum sativum*—(for example as supplied by Fragrance Oils (International) Ltd),
Thyme—*thymus vulgaris*—(for example as supplied by Cosmetochem International Ltd, Sennweidstrasse 44/46, CH-6312 Steinhausen,/ZG, Switzerland),
Rosehip—*rosa canina*—(for example example the Provital product as supplied by S Black Ltd).

The results of the in vivo tests described above for the above chain-breaking antioxidants when used at a level of 0.5% of the total weight of the composition are given in Table 1:

TABLE 1

| Antioxidant (0.5% by weight) | Inhibition of Lipid Peroxide development |
| --- | --- |
| Rosemary - *rosmarinus officinalis* | 27% |
| Oregano - *origanum vulgare* | 64% |
| Green Tea - *camellia sinensis* | 51% |
| Japanese Green Tea - *camellia oleifera* | 47% |
| Sage - *salvia officinalis* | 47% |
| Celery - *apium graveolens* | 51% |
| Thyme - *thymus vulgaris* | 26% |
| Rosehips - *rosa canina* | 13% |
| Coriander - *coriandrum sativum* | 37% |

The total amount of chain-breaking antioxidants used in the hair colouring compositions of the present invention may be in the range of 0.1%–5.0% by weight of the total weight of the composition, preferably in the range of 0.5%–1.5% of the total weight of the composition.

Combinations of two or three of the above show enhanced effects. The results of ex vivo tests described above for combinations of chain-breaking antioxidants are given below in Table 2. In these tests the a total amount of antoxidant present was 0.5% and equal amounts of each antioxidant were used [i.e. if 3 antioxidants were present, each was used at 0.167% (0.5%/3)]

TABLE 2

| Combination of Extracts | Observed inhibition of lipid peroxide development | Expected additive effect |
| --- | --- | --- |
| Rosemary + Oregano + Green Tea | 70% | 46% |
| Rosemary + Oregano + Sage | 71% | 46% |
| Rosemary + Sage + Celery | 71% | 41.6% |
| Rosemary + Thyme + Rosehip | 72% | 22% |
| Thyme + Oregano | 70% | 45% |
| Thyme + Oregano + Green Tea | 76% | 45.6% |
| Thyme + Coriander + Sage | 78% | 36.6% |
| Thyme + Coriander + Oregano | 77% | 42.3% |
| Rosehip + Oregano | 84% | 38.5% |
| Rosehip + Coriander + Green Tea | 80% | 33.6% |
| Rosehip + Japanese Green Tea + Thyme | 72% | 28.6% |

For all the examples given above, the effect observed with a combination of the antoxidants at a total level of 0.5% is far better than the expected additive effect. The expected additive effect is calculated as the sum of inhibition observed (See Table 1) for each individual antioxidant divided by the number of antioxidants in combination. For example, for a combination of three antioxidants the expected additive effect is given by the formula Inhibition of A at 0.5%/3+Inhibition of B at 0.5%/3+ Inhibition of C at 0.5%/3

Rosemary+Thyme+Rosehip=72% reduction in lipid peroxidation. This is greater than the additive effect, which is 22% reduction, so shows a synergistic effect. Expected additive reduction=(27/3)+(26/3)+(13/3)=22%.

Rosehip+Oregano=84% reduction in lipid peroxidation. This is greater than the additive effect, which is 38.5% reduction, so shows a synergistic effect. Expected additive reduction=(13/2)+(64/2)=38.5%.

Similarly for the other combinations, the observed effects are greater than the expected additive effect showing that the combinations are synergistic.

Certain antioxidants did not work, and actually induced more lipid peroxidation. This effect was also enhanced when these were in combination.

An example is Eucalyptus (+50%)+Passionflower (+116.5%)+Yarrow (+81.8%)=+202% more lipid peroxidation to the hair. Showing that the synergistic effects can also be replicated with the compounds that induced damage to the hair.

The present invention can be delivered to hair via any of the conventional formulation known to those skilled in the art, such as shampoos, conditioners (both emulsion and non-emulsion types), lotions (including developing lotions), sprays, gels, waxes, serums, mousses, tonics etc. Of these types of formulation, the range of ingredients can be broad. Such ingredients are surfactants, conditioning agents, waxes, thickeners, preservatives, and resins, sequestering agents, slip aids, vitamins, gelling agents, pearlising agents, pH adjusting agents and sunscreening agents.

The composition may include a surfactant such as cosmetically acceptable salts of alkyl ether sulphates (such as ammonium laureth sulphate or sodium laureth sulphate), alkyl and alkylamidoalkyl betaines (such as cocamidopropyl betaine), ethoxylated alcohols, polyethyleneglycol carboxylates, accepted salts of alkyl sulphates (such as ammonium lauryl sulphate or sodium lauryl sulphate), sulphosuccinates (such as disodium laureth sulphosuccinate), amphoacetates and amphodiacetates (such as disodium cocoamphodiacetates), alkylglucosides and alcohol sulphonates, incorporated in an amount of from about 1% to 99% by weight of the composition.

The composition may also include a thickener or viscosity controlling agent such as an amine oxide, block polymers of ethylene oxide and propylene oxide (for examples, those available from BASF Wyandotte under the trade name "Pluronic" RTM), ethoxylated fatty alcohols, cellulosic derivatives (such as hydroxypropylmethyl cellulose), salt (NaCl), phthalic acid amide, polyvinylalcohols and fatty alcohols, suitably in an amount from about 0.5% to about 10% by weight of the compostion.

Sequestering agents may be added to the composition, such as ethylenediamine tetraacetic acid (EDTA) and salts thereof, suitably in an amount of from about 0.005% to about 0.5% by weight of the composition.

Also included in the composition may be waxes such as cocoa butter, suitably in an amount of from about 0.01% to about 1.0% by weight of the composition. The composition may also include gelling agents such as PVM, MA or a decadiene crosspolymer (available under the trade name Stabilez 06), suitably in an amount from about 0.1% to 2.0% by weight of the composition.

Pearlising agents may be included eg stearic monoethanolamine, suitably in an amount from about 0.01% to about 10% by weight of the composition. The pH of the composition is generally required to be in the range of 8 to 12, preferably in the range of 9–10.5, for the desired performance as a permanent hair colour. To achieve this, the composition may need to be buffered using means well known in the art, such as a system comprising succinic acid, citric acid, lactic acid and acceptable salts thereof, phosphoric acid, mono or disodium phosphate and sodium carbonate. The pH may be adjusted with an agent such as sodium hydroxide, aminomethyl propanol, triethanolamine and caustic potash, suitably in an amount from about 0.01% to about 10% by weight of the composition.

If the composition is in the form of an emulsion, the emulsifiers used may be any emulsifiers known in the art for use in water-in-oil or oil-in-water emulsions, examples of which follow:
a) sesquioleates such as sorbitan sesquioleate, available commercially for example under the trade name Arlacel 83 (ICI), or polyglyceryl-2-sesquioleate;
b) ethoxylated esters of derivatives of natural oils such as the polyethoxylated ester of hydrogenated castor oil available commercially for example under the trade name Arlacel 989 (ICI);
c) silicone emulsifiers such as silicone polyols available commercially for example under the trade name ABIL WS08 (Th. Goldschmidt AG);
d) anionic emulsifiers such as fatty acid soaps eg potassium stearate and fatty acid sulphates eg sodium cetostearyl sulphate available commercially under the trade name Dehydag (Henkel);
e) ethoxylated fatty alcohols, for example the emulsifiers available commercially under the trade name Brij (ICI);
f) sorbitan esters, for example the emulsifiers available commercially under the trade name Span (ICI);
g) ethoxylated sorbitan esters, for example the emulsifiers available commercially under the trade name Tween (ICI);
h) ethoxylated fatty acid esters such as ethoxylated stearates, for example the emulsifiers available commercially under the trade name Myrj (ICI);
i) ethoxylated mono-, di-, and tri-glycerides, for example the emulsifiers available commercially under the trade name Labrafil (Alfa Chem.);
j) non-ionic self-emulsifying waxes, for example the wax available commercially under the trade name Polawax (Croda);
k) ethoxylated fatty acids, for example the emulsifiers available commercially under the trade name Tefose (Alfa Chem.); or
l) mixtures thereof.

The amount of emulsifier present in the water-in-oil compositions of the present disclosure is preferably in the range 0.1 to 10%.

The invention will be illustrated by the following Examples, which are given by way of example only. The "Antioxidant" in these Examples may be any one of the antioxidants referred to above or a combination of two or three of these antioxidants, eg the preferred combinations set out above. The type and amount of hair dye to be incorporated will depend on the colorant effect desired.

EXAMPLE 1

Surfactant (Shampoo) Base Component Carrying the Hair Dye Molecules

|   | % w/w |
|---|---|
| 1. Cocamide MEA | 3.5 |
| 2. Glycol Distrearate | 3.5 |
| 3. Sodium Gluceptate | 0.25 |
| 4. Sodium Metabisulfate | 2.0 |
| 5. Sodium Erthroborate | 0.3 |
| 6. Cocamidopropyl Betaine | 6.625 |
| 7. Dilute Sodium Lauryl-ether Sulfate | 25.75 |
| 8. Laureth-3 | 10 |
| 9. Oleic acid | 4 |
| 10. Ammonia | 3.5 |

-continued

|   | % w/w |
|---|---|
| 11. Citric acid monohydrate | 0.1 |
| 12. Hair Dyes | qs |
| 13. Antioxidant | 0.5% |
| 14. Purified water | to 100% |

Method
1. Heat 1, 2 & 8 to 70–75° C., until melted.
2. Disperse 3, 4, 5, 11 & 12 into 14 and heat to 70–75° C.
3. Stir in 6 & 7, to water phase, and maintain at 70–75° C.
4. Add oils phase to water phase and homogenise for 10 minutes.
5. Cool to <35° C.
6. Stir in 9 & 10 slowly, followed by 13.

EXAMPLE 2

Emulsion (Conditioner) Base Component Carrying the Hair Dye Molecules

|   | % w/w |
|---|---|
| 1. Tetra sodium EDTA | 0.14 |
| 2. Sodium Benzoate | 0.1 |
| 3. Phenoxyethanol | 0.1 |
| 4. Citric asid monohydrate | 1.5 |
| 5. Ceteath-25 | 1.5 |
| 6. Cetearyl alcohol | 2.25 |
| 7. Stearyl alcohol | 2.25 |
| 8. Hair dyes | qs |
| 9. Antioxidant | 0.5% |
| 10. Purified water | to 100% |

Method
1. Heat 5, 6 & 7 to 70–75° C.
2. Disperse 1, 2, 4 & 8 into 10. Heat to70–75° C.
3. Add oils to water phase and homogenise for 10 minutes.
4. Cool to <35° C.
5. Stir in 3, followed by 9.

EXAMPLE 3

Developing Lotion Component Carrying the Oxidising Agent

|   | % w/w |
|---|---|
| 1. Tetra sodium EDTA | 0.1 |
| 2. Phosphoric acid | 0.1 |
| 3. Hydrogen peroxide solution (65%) | 25.0 |
| 4. Ceteath-20 | 2.0 |
| 5. Cetearyl alcohol | 4.0 |
| 6. Sodium Stannate | 0.005 |
| 7. Antioxidant | 0.5% |
| 8. Purified water | to 100% |

Method
1. Disperse 1, 2 & 6 into 8. Heat to 70–75° C.
2. Heat 4 & 5 to 70–75° C. until melted.
3. Add oils to water and homogenise for 10 minutes.

4. Cool to <35° C.

5. Stir in 3, followed by 7.

In use, a conventional product combination would be the shampoo or conditioner base product (for example the formulation of Example 1 or Example 2) carrying the hair dye molecules and the developing lotion (for example the formulation of Example 3) that delivers the oxidising agent, which in the case of Example 3 is hydrogen peroxide, but could be another oxidising agent. Typically, equal volumes of the base formulation and the developing lotion are mixed together, to oxidatively activate the dye molecule to react with each other. This mixture is then applied to dry hair for any time from about 10 minutes to about 60 minutes. The hair is then rinsed with water and usually a shampoo or conditioner is used. This is followed by drying of the hair, naturally or by towel, or the use of a hair dryer. The chain-breaking antioxidant agents of the present invention can be included in either the base formulation, which carries the dyes (such as a shampoo-type formula, or a conditioner emulsion-type formula). Other types of carrier of the dye molecules and the chain-breaking antioxidants may be used such as mousses, foams, gels, creams, lotions and rinses, which may or may not be used in conjunction with a second component.

The invention claimed is:

1. Hair colouring composition containing an oxidative hair dye and two or more antioxidant agents, including one antioxidant selected from a first group consisting of

*origanum vulgare;*

*camellia sinensis;*

*camellia oleifera;*

*apium graveolens*; and

*salvia officinalis* and the other of said antioxidants is selected from a second group consisting of

*thymus vulgaris;*

*rosa canina*; and

*coriandrum sativum.*

2. Hair colouring composition as claimed in claim 1, wherein the antioxidant from the first group is *origanum vulgare.*

3. Hair colouring composition as claimed in claim 2, wherein the antioxidant from the second group is either *rosa canina* or *thymus vulgaris.*

4. Hair colouring composition as claimed in claim 1, which comprises three of said antioxidants.

5. Hair colouring composition as claimed in claim 1, wherein one or two of said antioxidants are selected from the first group defined in claim 1 and two or one respectively are selected from the second group defined in claim 1.

6. Hair colouring composition as claimed in claim 5, comprising one antioxidant from the first group and two from the second group.

7. Hair colouring composition as claimed in claim 6, wherein the two antioxidants from the second group are selected from *rosa canina, coriandrum sativum* and *thymus vulgaris.*

8. Hair colouring composition as claimed in claim 7, wherein the antioxidant from the first group is selected from the group consisting of

*camellia oleifera;*

*camellia sinensis;*

*salvia officinalis*; and

*origanum vulgare.*

9. Hair colouring composition as claimed in claim 8, wherein the composition comprises one of the following combinations of antioxidants:

*camellia oleifera/rosa canina/thymus vulgaris*

*camellia sinensis/rosa canina/coriandrum sativum*

*salvia officinalis/coriandrum sativum/thymus vulgaris*; and

*origanum vulgare/coriandrum sativum/thymus vulgaris.*

10. Hair colouring composition as claimed in claim 9, wherein the combination of antioxidants is *camellia oleifera/rosa canina/thymus vulgaris.*

11. Hair colouring composition as claimed in claim 1, wherein the total amount of antioxidant agents lies in the range of 0.1% to 5.0% of the total weight of the composition.

12. Hair colouring composition as claimed in claim 1, wherein the total amount of antioxidant agents present lies in the range of 0.5%–1.5% of the total composition by weight.

13. Hair colouring composition as claimed in claim 1, which exhibits a level of lipid peroxidation inhibition of greater than 60%.

14. Hair colouring composition as claimed in claim 1, wherein the hair dye is selected from the group consisting of p-amino phenol, p-phenylenediamine, 4-chlororesorcinol, resorcinol, p-amino-o-cresol, m-aminophenol, p-toluenediamine sulphate, N,N-bis(hydroxyethyl-p-phenylenediamine) sulphate, 2,5-diamine toluene sulphate, 4-amino-2-hydroxy toluene, 2-amino 4-hydroxyethylaminoanisole sulphate, o-chloro-p-phenylenediamine sulphate, 4-nitro-m-phenylenediamine, n-phenyl-p-phenylenediamine, n-phenyl-p-phenylenediamine sulphate, 1-naphthol, 6-chloro-2-amino-4-nitrophenol, 2-amino-3-hydroxy pyridine, 4-amino-3-nitrophenol, 4-amino-m-cresol, 2-methyl-5-hydroxyethylaminophenol, 6-hydroxyindole, 2-methyl resorcinol, 5-amino-6-chloro-o-cresol, 1-phenyl-3-methyl-5-pyrazolone, 4-hydroxypropylamino-2-nitrophenol, 4-hydroxyethlamino-2-nitrophenol, 2,6 diaminopyridine, m-phenylenediamine, p-aminophenol sulphate, m-aminophenol sulphate, phenyl methyl pyrazolone, 2,4-diaminophenoxyethanol HCl, t-butylhydroquinone, p-methyl aminophenol sulphate, 2-amino-3-hydroxypyridine, 4-amino-2-hydroxytoluene, p-methyl aminophenol sulphate, 2,6-dihydroxy-3,4-dimethylpuridine, and 1,2-bis-(2, 4-diaminophenoxy) propane or 1,5-naphthalenediol.

15. Hair colouring composition as claimed in claim 1, in the form of a formulation selected from the group consisting of shampoos, conditioners, lotions, sprays, gels, waxes, serums, mousses, and tonics.

16. Hair colouring composition as claimed in claim 15, further comprising one or more excipients selected from surfactants, conditioning agents, waxes, thickeners, preservatives, resins, sequestering agents, slip aids, vitamins, gelling agents, pearlising agents, pH adjusting agents and sunscreening agents.

17. Hair colouring composition as claimed in claim 1, which is in the form of a two-component formulation, a first component including one or more hair dyes and a second component including an oxidising agent.

18. Hair colouring composition as claimed in claim 1, which comprises hydrogen peroxide as oxidising agent.

19. A method of permanently or semi-permanently colouring hair by means of an oxidative process, which method comprises application to the hair of a hair colouring composition containing an oxidative hair dye and two or more antioxidant agents selected from the group consisting of

*rosmarinus officinalis;*
*oricianum vulpare;*
*camellia sinensis;*
*camellia oleifera;*
*salvia officinalis;*
*apium ciraveolen;*
*thymus vulparis;*
*rosa canina;* and
*coriandrum sativum*
in combination with a suitable diluent or carrier.

20. The method according to claim 19, wherein the composition comprises one of the following combinations of antioxidants:

*camellia oleifera/rosa canina/thymus vulgaris*
*camellia sinensis/rosa canina/coriandrum sativum*
*salvia officinalis/coriandrum sativum/thymus vulgaris*; and
*origanum vulgare/coriandrum sativum/thymus vulgaris.*

* * * * *